United States Patent
Kravitz et al.

(10) Patent No.: US 9,642,625 B2
(45) Date of Patent: May 9, 2017

(54) CANNULA FOR A DONOR ORGAN WITH OR WITHOUT AN AORTIC CUFF OR PATCH

(75) Inventors: David Kravitz, Barrington Hills, IL (US); Christopher Steinman, Sandy, UT (US); David Pettinato, Schaumburg, IL (US)

(73) Assignee: LIFELINE SCIENTIFIC, INC., Itasca, IL (US)

( * ) Notice: Subject to any disclaimer, the term of this patent is extended or adjusted under 35 U.S.C. 154(b) by 1435 days.

(21) Appl. No.: 13/283,166

(22) Filed: Oct. 27, 2011

(65) Prior Publication Data

US 2012/0277681 A1 Nov. 1, 2012

Related U.S. Application Data

(63) Continuation-in-part of application No. 13/097,789, filed on Apr. 29, 2011, now Pat. No. 9,022,978.

(51) Int. Cl.
*A61M 25/00* (2006.01)
*A61B 17/122* (2006.01)
*A61B 17/00* (2006.01)

(52) U.S. Cl.
CPC .. *A61B 17/122* (2013.01); *A61B 2017/00907* (2013.01); *A61B 2017/00969* (2013.01)

(58) Field of Classification Search
CPC . A01N 1/0247; A61M 39/284; A61M 1/1008; A61M 39/0247; A61M 39/28
USPC ................................. 604/250, 264
See application file for complete search history.

(56) References Cited

U.S. PATENT DOCUMENTS

| | | |
|---|---|---|
| 3,406,531 A | 10/1968 | Swenson et al. |
| 3,538,915 A | 11/1970 | Frampton et al. |
| 3,545,221 A | 12/1970 | Swenson et al. |
| 3,607,646 A | 9/1971 | de Roissart |
| 3,654,085 A | 4/1972 | Norr et al. |
| 3,660,241 A | 5/1972 | Michielsen |
| 3,738,914 A | 6/1973 | Thorne et al. |
| 3,777,507 A | 12/1973 | Burton et al. |
| 3,810,367 A | 5/1974 | Peterson |
| 3,843,455 A | 10/1974 | Bier |
| 3,877,843 A | 4/1975 | Fischel |

(Continued)

FOREIGN PATENT DOCUMENTS

| | | |
|---|---|---|
| DE | 38 08 942 | 9/1989 |
| DE | 43 24 637 A1 | 3/1995 |

(Continued)

OTHER PUBLICATIONS

"Organ Preservation", J.H. Southard, Ph.D. and F.O. Belzer, M.D., *Principles of Organ Transplantation*, Chapter 10, pp. 194-215, 1989.

(Continued)

*Primary Examiner* — Phillip Gray
(74) *Attorney, Agent, or Firm* — Oliff PLC

(57) ABSTRACT

A cannula includes a first circumferential portion, a second circumferential portion, and a seal with a first clamping surface. The first circumferential portion and the second circumferential portion are configured to mutually cooperate to support a circumference of vasculature, and form a second clamping surface. The first clamping surface and the second clamping surface are configured to cooperate to secure an end of the vasculature.

16 Claims, 6 Drawing Sheets

(56) References Cited

U.S. PATENT DOCUMENTS

| | | |
|---|---|---|
| 3,881,990 A | 5/1975 | Burton et al. |
| 3,892,628 A | 7/1975 | Thorne et al. |
| 3,914,954 A | 10/1975 | Doerig |
| 3,935,065 A | 1/1976 | Doerig |
| 3,995,444 A | 12/1976 | Clark et al. |
| 4,006,744 A | 2/1977 | Steer |
| 4,112,944 A | 9/1978 | Williams |
| 4,186,565 A | 2/1980 | Toledo-Pereyra |
| 4,242,883 A | 1/1981 | Toledo-Pereyra |
| 4,462,215 A | 7/1984 | Kuraoka et al. |
| 4,471,629 A | 9/1984 | Toledo-Pereyra |
| 4,473,637 A | 9/1984 | Guibert |
| 4,474,016 A | 10/1984 | Winchell |
| 4,494,385 A | 1/1985 | Kuraoka et al. |
| 4,502,295 A | 3/1985 | Toledo-Pereyra |
| 4,629,686 A | 12/1986 | Gruenberg |
| 4,723,974 A | 2/1988 | Ammerman |
| 4,745,759 A | 5/1988 | Bauer et al. |
| 4,766,740 A | 8/1988 | Bradley et al. |
| 4,800,879 A | 1/1989 | Golyakhovsky et al. |
| 4,837,390 A | 6/1989 | Reneau |
| 4,951,482 A | 8/1990 | Gilbert |
| 4,958,506 A | 9/1990 | Guilhem et al. |
| 5,004,457 A | 4/1991 | Wyatt |
| 5,051,352 A | 9/1991 | Martindale et al. |
| 5,141,847 A | 8/1992 | Sugimachi et al. |
| 5,149,321 A | 9/1992 | Klatz et al. |
| 5,157,930 A | 10/1992 | McGhee et al. |
| 5,217,860 A | 6/1993 | Fahy et al. |
| 5,285,657 A | 2/1994 | Bacchi et al. |
| 5,326,706 A | 7/1994 | Yland et al. |
| 5,338,662 A | 8/1994 | Sadri |
| 5,356,771 A | 10/1994 | O'Dell |
| 5,362,622 A | 11/1994 | O'Dell et al. |
| 5,383,854 A | 1/1995 | Safar et al. |
| 5,385,821 A | 1/1995 | O'Dell et al. |
| 5,395,314 A | 3/1995 | Klatz et al. |
| 5,434,045 A | 7/1995 | Jost |
| 5,472,876 A | 12/1995 | Fahy |
| 5,476,763 A | 12/1995 | Bacchi et al. |
| 5,494,822 A | 2/1996 | Sadri |
| 5,496,289 A | 3/1996 | Wenstrom, Jr. |
| 5,586,438 A | 12/1996 | Fahy |
| 5,681,740 A | 10/1997 | Messier et al. |
| 5,709,654 A | 1/1998 | Klatz et al. |
| 5,723,282 A | 3/1998 | Fahy et al. |
| 5,728,115 A | 3/1998 | Westcott et al. |
| 5,752,929 A | 5/1998 | Klatz et al. |
| 5,814,016 A | 9/1998 | Valley et al. |
| 5,821,045 A | 10/1998 | Fahy et al. |
| 5,856,081 A | 1/1999 | Fahy |
| 5,965,433 A | 10/1999 | Gardetto et al. |
| 6,014,864 A | 1/2000 | Owen |
| 6,046,046 A | 4/2000 | Hassanein |
| 6,183,019 B1 | 2/2001 | Owen |
| 6,241,945 B1 | 6/2001 | Owen |
| 6,355,010 B1 | 3/2002 | Barbut |
| 6,485,450 B1 | 11/2002 | Owen |
| 6,626,869 B1 | 9/2003 | Bint |
| 6,726,651 B1 | 4/2004 | Robinson et al. |
| 7,678,563 B2 | 3/2010 | Wright et al. |
| 2004/0111104 A1* | 6/2004 | Schein ............... A61B 17/00 606/153 |
| 2004/0221719 A1 | 11/2004 | Wright et al. |
| 2006/0247498 A1 | 11/2006 | Bonadio et al. |
| 2008/0086080 A1 | 4/2008 | Mastri et al. |
| 2011/0059429 A1 | 3/2011 | Owen et al. |

FOREIGN PATENT DOCUMENTS

| | | |
|---|---|---|
| EP | 0 096 997 | 12/1983 |
| EP | 0 376 763 A2 | 7/1990 |
| EP | 2 218 407 A1 | 8/2010 |
| JP | 2-258701 | 10/1990 |
| SU | 760972 | 9/1980 |
| WO | WO 91/03934 | 4/1991 |
| WO | WO 91/14364 | 10/1991 |
| WO | WO 93/00808 | 1/1993 |
| WO | WO 96/05727 | 2/1996 |
| WO | WO 96/13288 | 5/1996 |
| WO | WO 96/29865 | 10/1996 |
| WO | WO 96/30111 | 10/1996 |
| WO | WO 97/45527 | 12/1997 |
| WO | WO 99/15011 | 4/1999 |
| WO | WO 00/18226 | 4/2000 |
| WO | WO 02/26034 A | 4/2002 |
| WO | WO 2006/105444 A2 | 10/2006 |
| WO | WO 2008/017329 A1 | 2/2008 |

OTHER PUBLICATIONS

"Organko Servierungsmachine OKM 82", Von Dietmer Scholz et al., East German Article, 1983 (with English Translation).

"Preservation of Cerebral Function During Circulatory Arrest and Resuscitation: Hypothermic Protective Considerations", Robert J. White, *Resuscitation*, vol. I, pp. 107-115, 1972.

"Storage and Transport of Heart and Heart-Lung Donor Organs With Inflatable Cushions and Eutectoid Cooling", D.R. Wheeldon et al., *The Journal of Heart Transplantation*, vol. 7, pp. 265-268, 1988.

"MOX®-100 Renal Preservation System", Waters Instruments Medical Group, pp. 2-7, 1982.

"Organ Perfusion Systems: An Evaluation Criteria", Fereydoon Sadri, Ph.D., *T.O.P.S. Medical Corporation*, pp. 1-8, 1987.

Gauke Kootstra et al, "A New Device Towards Intermediate Term Kidney Preservation—An Experimental Study," 1980, pp. 86-89.

U.S. Appl. No. 08/484,601, filed Jun. 7, 1995.

Feb. 27, 2014 Office Action issued in U.S. Appl. No. 13/097,789.

Jul. 22, 2013 International Preliminary Report on Patentability with Annex issued in International Application No. PCT/US2012/033234.

Jun. 9, 2015 Office Action issued in Chinese Application No. 201280030999.3.

Sep. 4, 2012 International Search Report issued in Application No. PCT/US2012/033234.

Sep. 4, 2012 Written Opinion issued in Application No. PCT/US2012/033234.

Oct. 25, 2016 Office Action issued in Chinese Patent Application No. 201280030999.3.

Mar. 14, 2016 Office Action issued in Chinese Patent Application No. 201280030999.3.

* cited by examiner

CANNULA FOR A DONOR ORGAN WITH OR WITHOUT AN AORTIC CUFF OR PATCH

This is a Continuation-in-Part of application Ser. No. 13/097,789 filed Apr. 29, 2011. The prior application, including the specification, drawings and abstract is incorporated herein by reference in its entirety.

BACKGROUND

I. Related Technical Fields

Related technical fields include cannulas and clamping methods, and more specifically, cannulas and clamping methods for perfusing one or more organs to monitor, treat, sustain and/or restore the viability of the organ(s) and/or for transporting and/or storing the organ(s).

II. Related Art

Various devices have been developed that couple the anatomy of an organ being perfused to a machine or other equipment. Such devices are typically referred to as perfusion clamps or simply cannulas. Although the term cannula in general use has other meanings, the term cannula is used generically throughout the specification to refer to a clamp or other device that provides a connection through which a fluid flow may be established.

A type of cannula as described in U.S. Pat. No. 5,728,115 to Westcott et al., which is hereby incorporated by reference, is shown in FIGS. 1-3. A clamping device (cannula) 10 is used to couple the perfusion cannula to the renal aorta 34. The clamp 10 includes two longitudinal members 12 and 14 which pivot about a pin 16. The proximal end of the member 12 includes an integral handle 18, while the proximal end of the member 14 includes an integral handle 20. The distal end of the member 12 includes an elongated, hollow, annular, integral clamp head 24, while the distal end of the member 14 includes an elongated, hollow, annular, integral clamp head 26. Clamp head 26 includes a nipple 28 attached thereto. Movement of the handles 18 and 20 toward one another forces the members 12 and 14 to pivot about the pin 16, thereby forcing the clamp heads 24 and 26 of the members 12 and 14 away from one another. A spring 22 is positioned between the handles 18 and 20 in order to bias the handles apart. This, in turn, tends to force the clamp heads 24 and 26 together. Therefore, the clamp heads 24 and 26 of the distal ends of the members 12 and 14 are engaged in a clamping relationship unless an external compressive force is applied to the handles 18 and 20. A lumen 32 extends through the nipple 28.

In use, the clamp 10 is attached to the renal aorta 34 of a donor organ such as a kidney 36 by opening the clamp 10, passing the distal end 38 of the renal aorta 34 through the annular clamp head 24, holding the distal end 38 of the renal aorta 34 over the annular clamp head 24, and releasing pressure on the handles of the clamp 10 in order to allow the clamp head 26 to engage the distal end 38 of the renal aorta 34 against the annular clamp head 24. A catheter 40 may then be attached to the nipple 28 in order to provide perfusion of liquid through the lumen 32 and into the renal aorta 34

U.S. Patent Application Publication No. 2004/0111104 to Schein et al., which is hereby incorporated by reference, discloses another type of cannula.

SUMMARY

The cannulas as described above require the use of an aortic patch also known as a Carrel patch, or cuff. An aortic patch is a section of the aorta that remains attached to the organ when the organ is removed from an organ donor. The aortic patch is used to facilitate cannulation of vasculature of the donated organ. An aortic patch is typically only available from a deceased donor because of the resultant damage to the aorta required for an aortic patch. As such, the cannulas described above suffer from a problem in that they are not suitable for use with organs, such as a kidney, donated from a living donor or organs where an aortic patch is otherwise not available. With such an organ, the amount of tissue available for cannulation is much less. Care must be taken not to damage the limited amount of tissue available when attaching a cannula so that adequate tissue remains to reconnect the organ when the organ is transplanted to the recipient, and to prevent damage that could result in loss of the organ.

Exemplary implementations of the broad inventive principles described herein provide a cannula that can be used without an aortic patch. Exemplary implementations provide a cannula with a first circumferential portion, a second circumferential portion; and a seal with a first clamping surface. The first circumferential portion and the second circumferential portion are configured to mutually cooperate to support a circumference of vasculature and form a second clamping surface. The first clamping surface and the second clamping surface are configured to cooperate to secure an end of the vasculature. These exemplary implementations provide a solution to problems and disadvantages discussed above because the exemplary implementations do not require an aortic patch and only engage a minimal amount of tissue.

Exemplary implementations of the broad inventive principles described herein provide a method of cannulating vasculature of an organ. The method includes enclosing a circumference of the vasculature with a first circumferential portion of a cannula and a second circumferential portion of the cannula to support the vasculature while maintaining a capability to flow liquid through the vasculature. The method includes contacting an end of the vasculature with a sealing portion of the cannula in a manner that maintains the capability to flow liquid through the vasculature to ensure a substantially leak free condition during perfusion. These exemplary implementations provide a solution to problems and disadvantages discussed above because the exemplary implementations do not require an aortic patch and only engage a minimal amount of tissue.

Exemplary implementations of the broad inventive principles described herein provide a cannula with an optically clear portion configured to allow a user to view at least one portion of an interior of vasculature and a seal when the cannula is in a position in which an end of the vasculature is secured by the cannula. The optically clear portion provides optical magnification of the artery in relation to its position in the cannula. These exemplary implementations provide a solution to problems and disadvantages discussed above because they allow for inspection of the vasculature for damage and proper connection while cannulated. The magnification may also allow the clinician to observe for trapped air bubbles or clots, or to observe the intima of the artery for damage Also, these exemplary implementations require less tissue from the vasculature to be used because the tissue can be readily viewed in the cannula to confirm that the cannula is properly connected. Thus, excess tissue does not need to be used in order to confirm that the tissue is properly cannulated.

BRIEF DESCRIPTION OF THE DRAWINGS

Exemplary implementations can be described with reference to the following figures wherein.

DETAILED DESCRIPTION OF EMBODIMENTS

Preservation of organs by machine perfusion has been accomplished at hypothermic temperatures with or without computer control with crystalloid perfusates and without oxygenation. See, for example, U.S. Pat. Nos. 5,149,321, 5,395,314, 5,584,804, 5,709,654 and 5,752,929 and U.S. patent application Ser. No. 08/484,601 to Klatz et al., which are hereby incorporated by reference.

Ideally organs would be procured in a manner that limits their warm ischemia time to essentially zero. Unfortunately, in reality, many organs, especially from non-beating heart donors, are procured after extended warm ischemia time periods (i.e. 45 minutes or more). The machine perfusion of these organs at low temperature has demonstrated significant improvement (Transpl Int 1996 Daemen). Numerous control circuits and pumping configurations have been utilized to achieve this objective and to machine perfuse organs in general. See, for example, U.S. Pat. Nos. 5,338,662 and 5,494,822 to Sadri; U.S. Pat. No. 4,745,759 to Bauer et al.; U.S. Pat. Nos. 5,217,860 and 5,472,876 to Fahy et al.; U.S. Pat. No. 5,051,352 to Martindale et al.; U.S. Pat. No. 3,995,444 to Clark et al.; U.S. Pat. No. 4,629,686 to Gruenberg; U.S. Pat. Nos. 3,738,914 and 3,892,628 to Thome et al.; U.S. Pat. Nos. 5,285,657 and 5,476,763 to Bacchi et al.; U.S. Pat. No. 5,157,930 to McGhee et al.; and U.S. Pat. No. 5,141,847 to Sugimachi et al., which are hereby incorporated by reference.

The cannulas and clamping methods described herein may be used in conjunction with apparatus and methods described in U.S. Pat. Nos. 6,014,864, 6,183,019, 6,241,945 and 6,485,450 to Owen, which are hereby incorporated by reference. While these apparatus and methods are related to organ recovery and transplantation, the cannulas and clamping methods described herein may also be used in various other medical procedures and with various other medical equipment where clamping with fluid flow is desired. Thus, the cannulas and clamping methods described herein are not limited to the applications described below in conjunction with the exemplary implementations.

Figure 1:
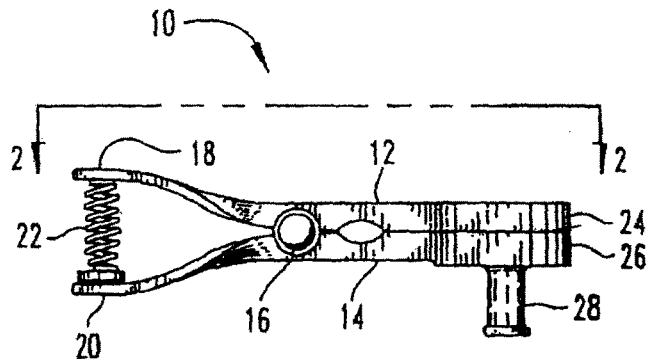
FIGS. 1-3 illustrate a cannula of the prior art.
Figure 2:
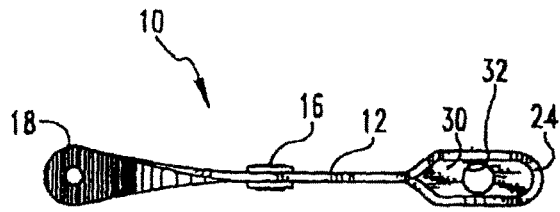
Figure 3:
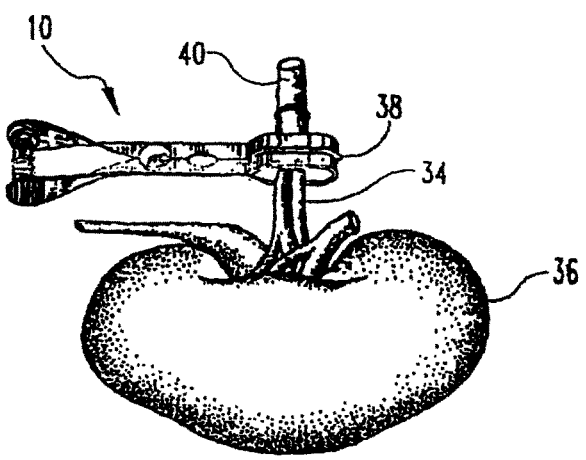
Figure 4:
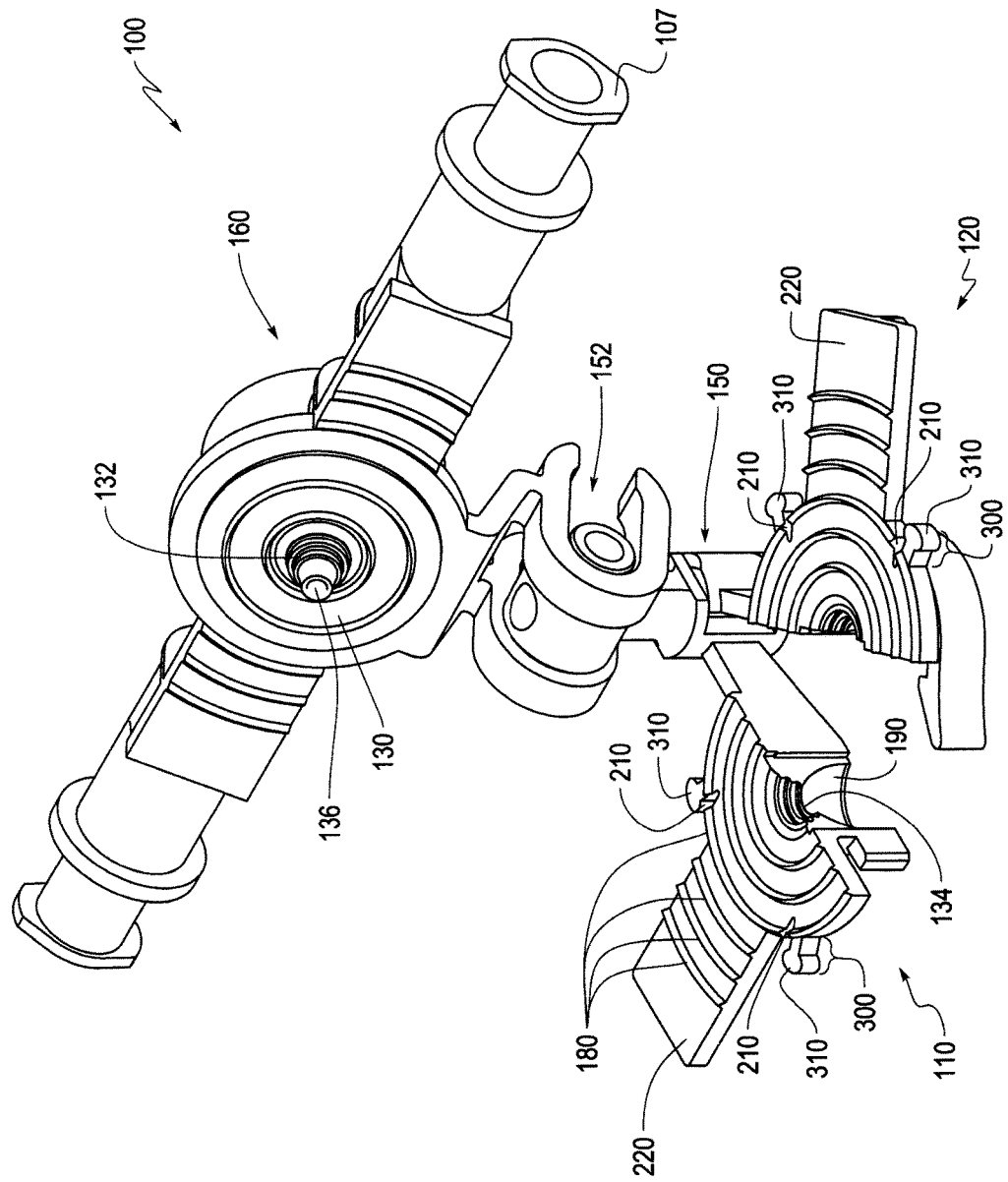
FIG. 4 illustrates a cannula in an open state.

FIG. 4 shows a perfusion clamping apparatus or cannula 100 according to a first exemplary implementation. The cannula 100 is capable of connecting one or more arteries of an organ to a perfusion machine or system (not shown), for example, by connection to tubing of the perfusion machine or system. All medical fluid contact surfaces are preferably formed of or coated with materials compatible with the medical fluid used, preferably non-thrombogenic materials.

The medical fluid for perfusion may be any suitable medical fluid. For example, it may be a simple crystalloid solution, or may be augmented with an appropriate oxygen carrier. The oxygen carrier may, for example, be washed, stabilized red blood cells, cross-linked hemoglobin, pegolated hemoglobin or fluorocarbon based emulsions. The medical fluid may also contain antioxidants known to reduce peroxidation or free radical damage in the physiological environment and specific agents known to aid in tissue protection. Further, the medical fluid may also include blood or blood products.

Figure 5:
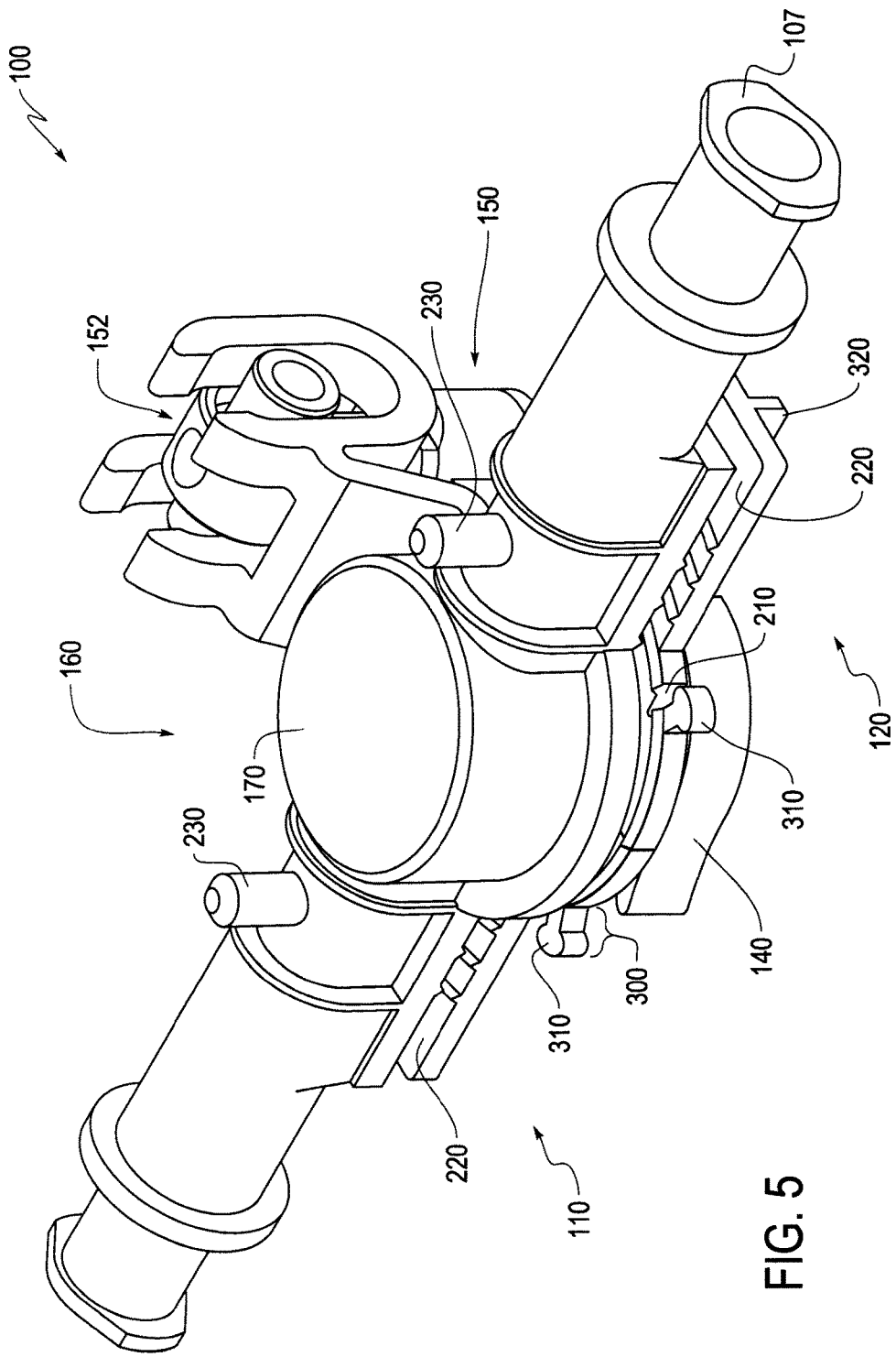
FIG. 5 illustrates a cannula in a closed state.

The cannula 100 is shown in FIG. 4 in an open condition and in FIG. 5 in a closed condition. In the open condition, a first circumferential portion 110 and a second circumferential portion 120 are rotated away from one another on a first hinge 150. The first and second circumferential portions are rotated into contact with one another to form a second clamping surface 134 (described later). When vasculature is disposed between the first circumferential portion 110 and second circumferential portion 120 in such a closed condition, the circumference of the vasculature is supported. A fastening structure 140 secures the first circumferential portion 110 and the second circumferential portion 120 in this closed condition. The fastening structure 140 can be achieved in numerous ways. In the figures, the fastening structure 140 is shown as a releasable snap fit, but other fastening structures, such as a strap or tie will have similar effect. When a releasable snap fit is used, the cannula can be reopened without breaking so that the vasculature can be trimmed or repositioned. Preferably, the releasable snap fit generates an audible sound such as a "click" when the snap fit is fully engaged, which allows the user to know that the snap fit is fully engaged without the need to perform a visual inspection.

Although the first circumferential portion 110 and the second circumferential portion 120 are shown as rotatably connected at the first hinge 150, other methods of connection are contemplated by the broad inventive principles described herein. For example, at least one of the first circumferential portion 110 and the second circumferential portion 120 could be unattached before closure, and then snap fitted to the other of the first circumferential portion 110 and the second circumferential portion 120. Alternatively, first circumferential portion 110 and the second circumferential portion 120 could translate on pins or rails. Many implementations of relative movement between these two parts are within the broad inventive principles described herein.

Figure 6:
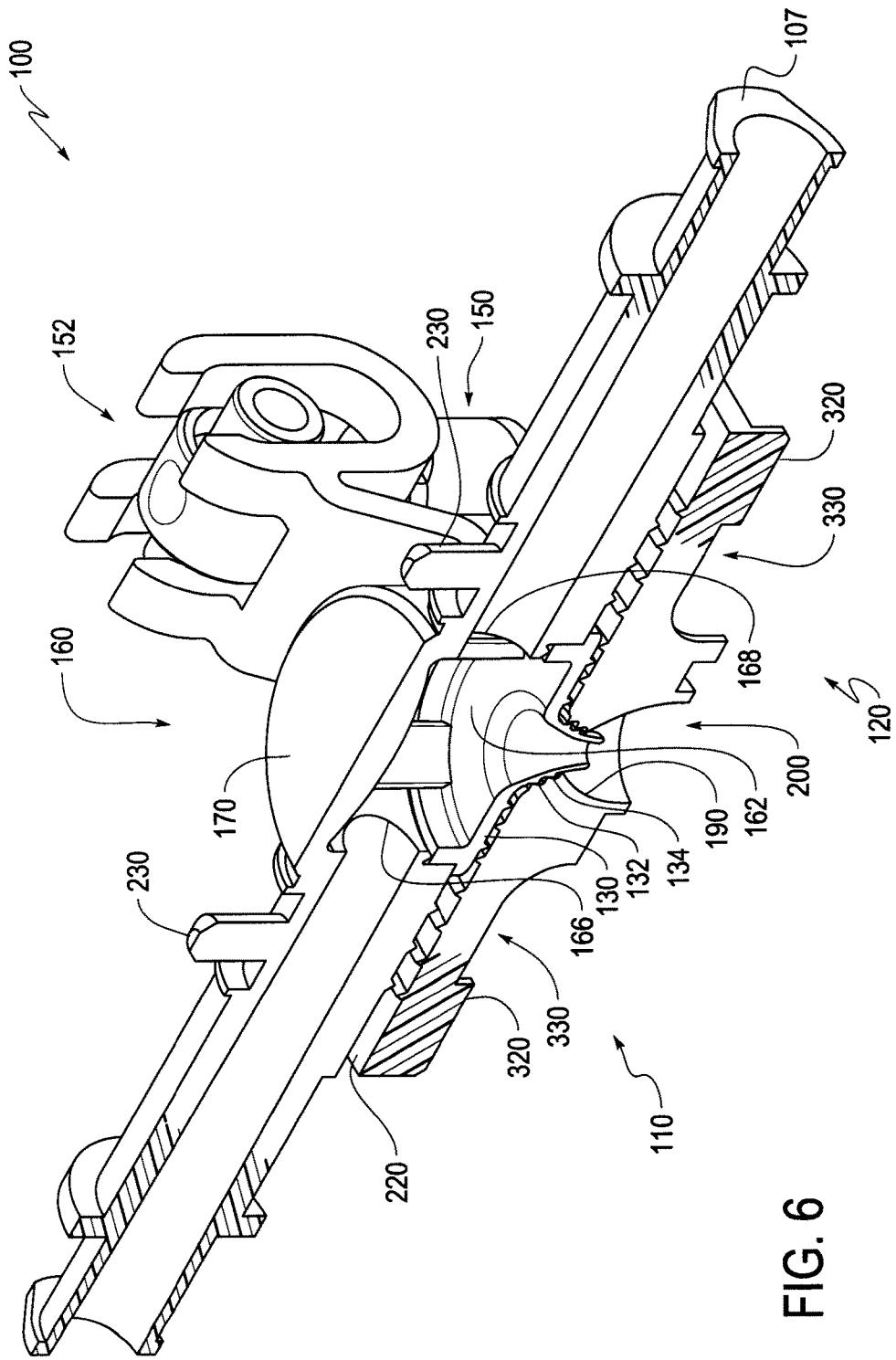
FIG. 6 illustrates a cross section of a cannula in a closed state.

Both of the first circumferential portion 110 and the second circumferential portion 120 include a tapered portion 190. As shown in FIG. 6, the tapered portion 190 is narrower in diameter than the cylindrical space 200 formed between the first circumferential portion 110 and the second circumferential portion 120. The tapered portion 190 helps to secure the vasculature, but should not excessively constrict fluid flow through the vasculature. To allow adequate fluid flow within the vasculature, the tapered portion 190 may constrict an outer diameter of the vasculature, for example, less than about twenty five percent, preferably less than twenty percent, for example about twelve or about nineteen percent at a narrowest point at or near the first clamping surface 132 and/or the second clamping surface 134. The tapered portion 190 preferably expands rapidly to the cylindrical portion 200 such that the cylindrical portion 200 results in minimal or zero interference with the vasculature. Such a configuration minimizes or completely avoids undue stenosis caused to the vasculature where it is not required.

After the vasculature is supported between the first circumferential portion 110 and the second circumferential portion 120, a seal 130 is brought into contact with an end of the vasculature. This can be achieved by rotating a chamber portion 160, via a second hinge 152, into a closed position (as shown in FIG. 5), which will bring the seal 130 into contact with an end of the vasculature. In this closed position, the first clamping surface 132 and the second clamping surface 134 secure and end of the vasculature. The complementary conical surfaces of a first clamping surface 132 and the second clamping surface 134 secure the end of the vasculature in a manner that allows free flow of liquid to an interior of the vasculature. Of course, other implementations of movement that secure the end of the vasculature are within the broad inventive principles described herein.

Figure 7:
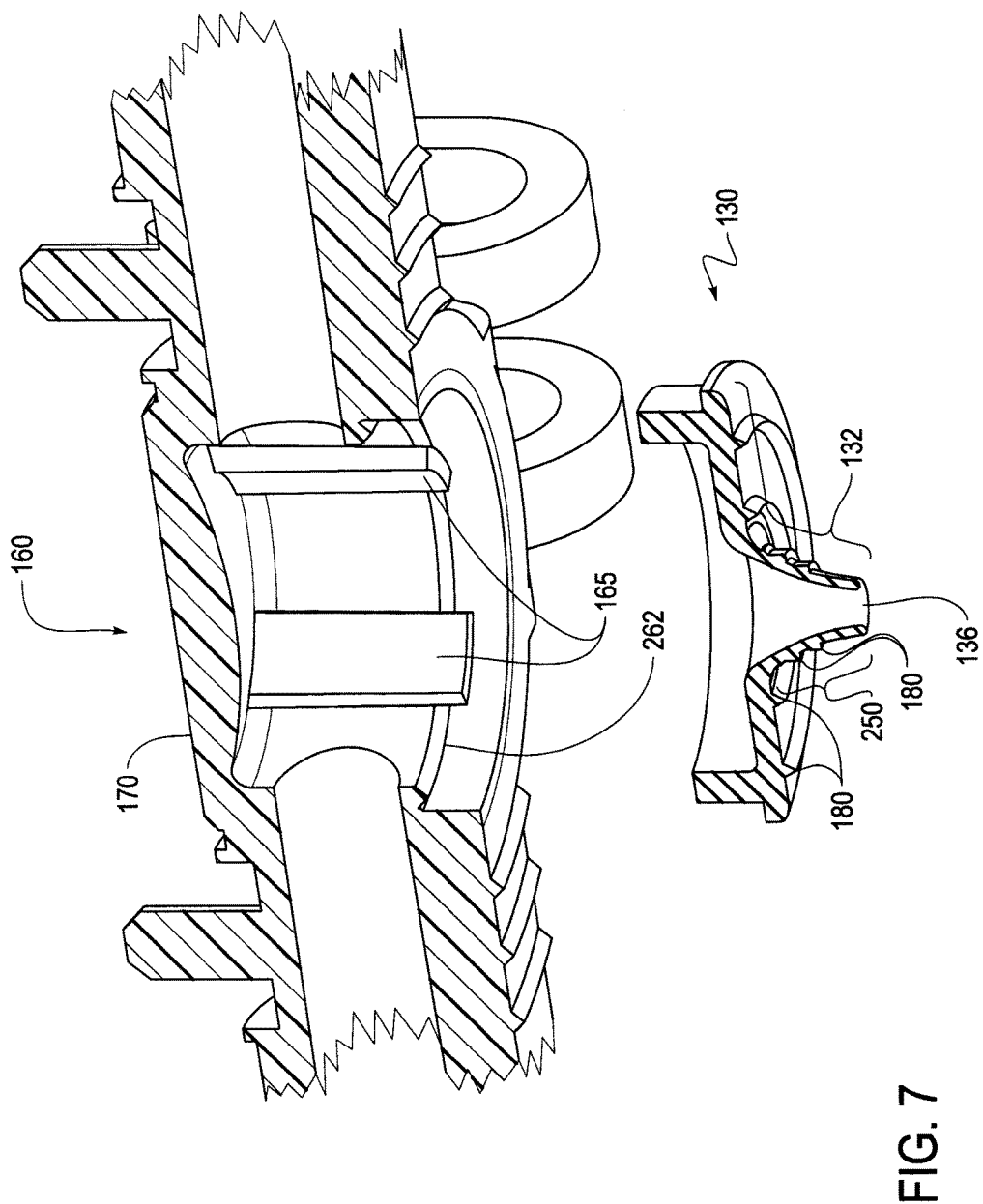
FIG. 7 illustrates a partial cross section of a cannula.

Free flow to and from an interior of the vasculature can be achieved by a flow passage 136. The flow passage 136 may be a circular hole through the seal 130, which may also be circular. The shape of the seal 130 and flow passage 136 are not limited to being circular, and may be influenced by other design considerations. The seal 130 may include a conical portion 250 at the flow passage 136 as shown in FIG. 7. The conical portion 250 may include serrations and/or knurls 180, which provide a labyrinth effect with complementary serrations and/or knurls 180 on the first circumferential portion 110 and/or the second circumferential portion 120, to improve the ability of the seal to secure the end of the vasculature. In one exemplary implementation, the conical portion 250 extends approximately 1.5 to 3.0 millimeters.

The seal 130 may be made of an elastomeric material. This will help to prevent damage to the vasculature, particularly an interior of the vasculature, which may be more susceptible to damage than an exterior of the vasculature. The shore A hardness (also known as the durometer) of the seal 130 can be chosen to be within a range of not less than about 32 and not greater than about 80 or within any smaller range therein, such as, not less than about 60 and not greater than about 70. As examples, the durometer can be about 35, 40, 45, 50 55, 60, 65, 70, 75 or 80. As used herein, the term "about" is intended to account for inherent manufacturing tolerances and inaccuracy in measurement. The hardness may be further tailored within or outside of these ranges depending upon the needs of the vasculature to be cannulated. Seals 130 of various hardness and/or seals 130 with different sizes of the flow passage 136 may be included with the cannula 100 to form a kit that can be used with different vasculatures.

The seal 130 is mated with a first opening (not labeled) in a chamber 162 of the chamber portion 160. The flow passage 136 allows liquid communication from the vasculature to the chamber 162. The chamber portion 160 also includes a second opening 166 and a third opening 168 in fluid communication with the chamber. The second opening 166 and the third opening 168 provide a "lateral" fluid flow, i.e., a flow of fluid that is substantially perpendicular to the direction of fluid flow to and from the tissue to which the cannula is attached. For example, the one or more fittings of the cannula are oriented to have an axis of fluid flow that is substantially perpendicular to an axis of fluid flow into/out of the flow passage 136. This "lateral" fluid flow arrangement allows the cannula to be connected to tubing of an organ transporter, for example, that is substantially in a single plane, for example, as described in U.S. Pat. No. 7,678,563 and U.S. Patent Application Publication No. 2004/0221719, both of which are hereby incorporated by reference. Further, multiple cannulas may be connected and even interconnected within substantially the same plane.

One or both of the second opening 166 and the third opening 168 may be connected to a fitting 107 utilized for priming and/or air bubble removal. A second fitting 107 comprises a port or valve for such purpose. The second opening 166 and the third opening 168 may be may also be used to network multiple cannulas, for example, by connecting tubing in parallel, for example, by running a split infuse line to the first fitting of each cannula, or in series, for example, by connecting the first fitting of a cannula to the second fitting of another cannula. Standard luer geometry or other suitable structure may be used for the fittings.

The chamber portion 160 may include an optically clear portion 170. The optically clear portion 170 allows for visual inspection of the interior of the cannula. This is particularly advantageous in that it allows a user to inspect the clamping of vasculature within the cannula and to inspect for other things such as damage to the vasculature or bubbles within or flowing through the cannula. The optically clear portion may provide optical magnification to allow the user to see more detail of the vasculature, which can be relatively small, perhaps three to seven millimeters in diameter.

The chamber portion 160 may include a seal engaging portion 262 disposed on a wall of the chamber portion and configured to engage an outer periphery of the seal 130. An exemplary engaging portion as shown in FIG. 7 is generally ridge-shaped, but can be any shape that facilitates a positive engagement with the seal 130. The seal engaging portion 262 can significantly improve the function of the seal 130. The chamber portion 160 may also include supports 165 that support the seal 130 and prevent the seal 130 from excessive flexure or even collapse. FIG. 7 shows a cross-section with two such supports 165 with an approximately rectangular cross section with an additional two supports 165 not visible, but any number of supports with any shape is encompassed by the broad inventive principles described herein. The supports 165 are shown closer to a center of the chamber portion 160 than the seal engaging portion 262, and the supports 165 are equally and radially spaced about a center of the chamber portion 160, which also corresponds to a center of the seal 130. Such supports reduce or completely avoid the possibility that a seal 130 made from a relatively soft elastomeric material can be turned "inside-out" within the chamber 160, which can prevent the seal 130 from properly performing its sealing function.

As shown in FIG. 4, both the first circumferential portion 110 and the second circumferential portion 120 include a surface 220 that is outside a diameter of the second clamping surface 134 and is approximately perpendicular to a circumference of a vasculature that is supported within the first circumferential portion 110 and the second circumferential portion 120. This surface includes serrations and/or knurls 180. Such serrations and/or knurls 180 may be included to secure additional tissue of the vasculature. Opposite the surface 220, a longitudinal stiffening rib 320 may be provided to improve the rigidity of the surface 220 as shown in FIG. 6. Although the cannula 100 is fully operational when securing vasculature without an aortic patch, the surface 220 and serrations and/or knurls 180 cooperate with corresponding structure (not labeled) on the chamber portion 160 to optionally secure an aortic patch. Thus, exemplary implementations of the broad inventive principles described herein provide for a cannula that can be used with or without an aortic patch. For example, when a kidney is cannulated, significant portions of the renal artery may or may not be present. Thus, the cannula 100 can be effectively used in either situation.

Serrations and/or knurls 180 may also be included on the second clamping surface 134. The serrations and/or knurls 180 may be omitted from the first clamping surface 132, particularly if contact from the first clamping surface 132 with an interior of the vasculature would otherwise cause unacceptable damage to the vasculature. The relatively soft elastomeric material of the seal 130 (and therefore of the second clamping surface 132) can help to prevent damage to the interior surface of the vasculature even if the serrations and/or knurls 180 are present on the seal 130. The length of the seal that enters the intima of the artery is minimized, therefore minimizing damage to the inside of the artery.

A notch 210 may also be included in one or both of the first circumferential portion 110 and the second circumferential portion 120. Four such notches are shown in FIG. 4. Each notch 210 may be used to secure sutures or side branches of the vasculature. The sutures may be attached to the side branches.

One or more cleat 300 may also be included in one or both of the first circumferential portion 110 and the second circumferential portion 120. Four such cleats distributed equidistant about the circumferential portions (for example, every ninety degrees) are shown in FIG. 4, but any number of cleats can be provided with any spacing. Each cleat 300 may be used, for example, to secure sutures or side branches of the vasculature. The sutures may be attached to the side branches. Such cleats can be configured such that the suture or side branches can be wrapped around or tied to the cleat. A preferred cleat is a protrusion that is generally post shaped. Preferably the post shape may include an enlarged portion 310, along the length or at the end of the post, such that the enlarged portion 310 is shaped and located so that the enlarged portion 310 provides an impediment to the suture or side branch sliding off of the cleat. Preferably the cleat 300 is configured for the suture or side branch to be attached to the cleat 300 between the enlarged portion 310 and on whichever of the first circumferential portion 110 and the second circumferential portion 120 the cleat 300 is included. The cleat 300 is shown with a generally rectangular or square cross section, but the cross section can be any shape as necessary to promote ease of use and/or ease of manufacturing.

Figure 8:
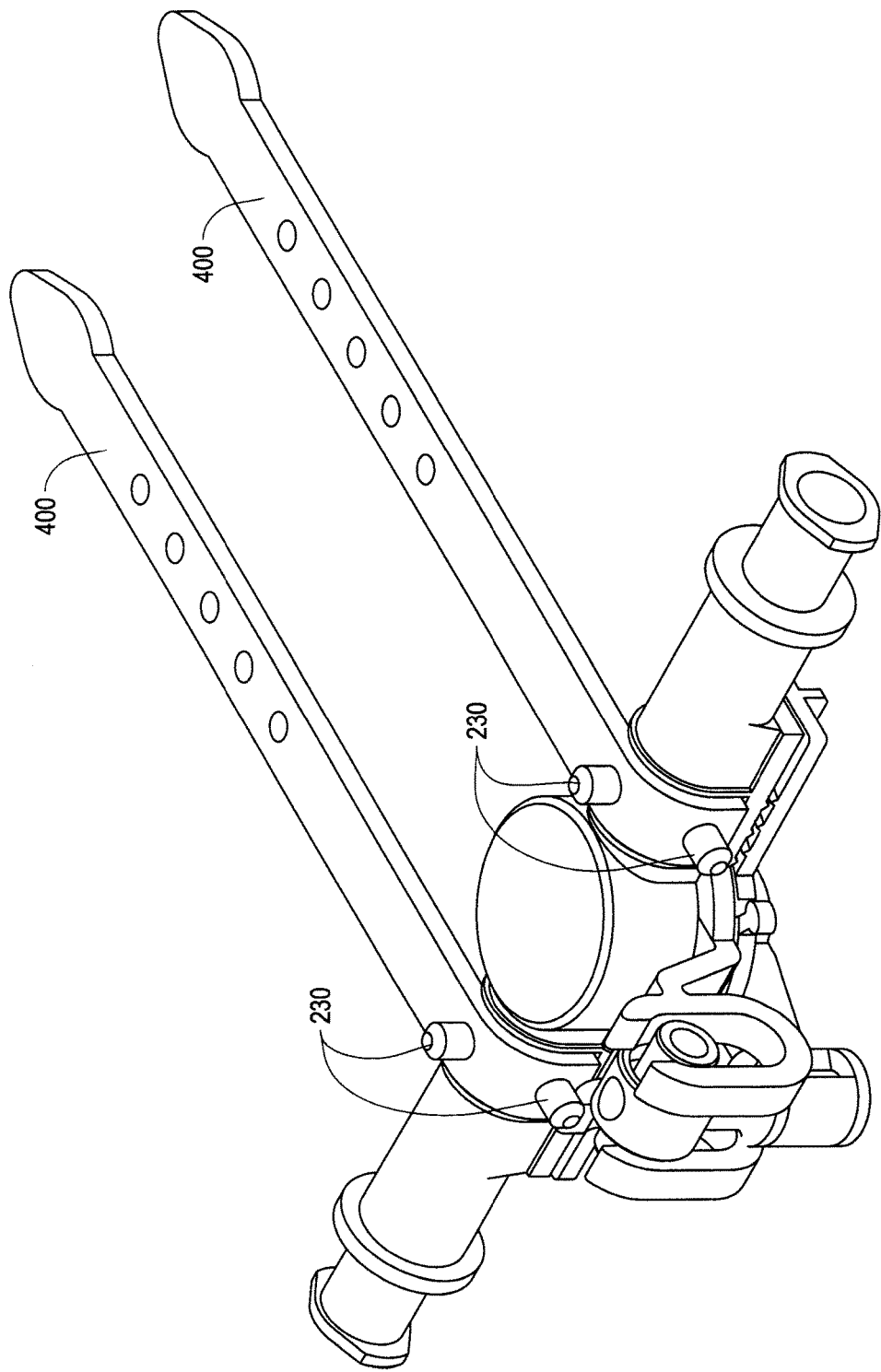
FIG. 8 illustrates a cannula in a closed state.

FIG. 5 includes four posts 230. These posts may be used to anchor one or more straps 400 that wrap around the cannula 100 to fasten the chamber portion 160 to the first circumferential portion 110 and the second circumferential portion 120 and keep the cannula in a closed state. A single post 230 can be used to anchor each strap 400, but if two or more posts 230 are included, ease of manufacturing and use can be improved and/or manufacturing costs can be decreased because the straps 400 can be fastened to the chamber portion 160 without the use of additional fastening structure such as adhesive. FIG. 5 shows two groups of two posts 230. In the exemplary embodiment of FIG. 8, each post 230 in each group of posts is disposed approximately ninety degrees around a surface of the cannula from one another. That is, the posts 230 in each group are approximately perpendicular to one another, but other relative positions are contemplated. Preferably the relative positions of the posts 230 in each group are chosen such that the strap 400 attached to each group of posts 230 to eliminate the need for adhesive. If a strap 400 is included, the stiffening rib 320 may include a recess 330 to facilitate location of the strap 400 and inhibit or prevent the strap from moving laterally. Alternative structures may also be used to fasten the chamber portion 160 to the first circumferential portion 110 and the second circumferential portion 120, such as a snap fit or ratcheting mechanism.

In an exemplary implementation, both the first hinge 150 and the second hinge 152 may include some stiffness or resistance to movement such that both of the hinges will remain in any partially or fully opened or closed state unless an external force is applied. Such stiffness or resistance can be achieved in the hinges by providing an interference fit or line-to-line fit in mating portions of the hinges. This facilitates ease of use because a user can place the hinges in any desired position without the hinges moving to an undesired position, which may free the user to hold the cannula in only one hand and allow the user's second hand to be free for other tasks.

While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying inventive principles.

What is claimed is:
1. A cannula comprising:
a first clamping surface;
a second clamping surface opposed to the first clamping surface,
the second clamping surface including a first circumferential portion and a second circumferential portion, and
the first circumferential portion and the second circumferential being rotatable about a first hinge to surround a length of vasculature such that a portion of the vasculature can pass between the first circumferential portion and the second circumferential portion and at least partially through the first clamping surface; and
a fastener configured to fasten the cannula to at least one of a side branch of the vasculature and a suture disposed on at least one of the vasculature and an organ.
2. The cannula according to claim 1, wherein the fastener comprises at least one notch disposed on a periphery of the second clamping surface.
3. The cannula according to claim 1, wherein the fastener comprises at least one protrusion extending from a periphery of the second clamping surface, the protrusion being configured to permit at least one of the side branch and the suture to be wrapped around the protrusion.
4. The cannula according to claim 3, wherein the protrusion comprises an enlarged portion that is configured to prevent the suture or the side branch from sliding off of the protrusion when the suture or the side branch is fastened to the protrusion between the periphery of the second clamping surface and the enlarged portion.
5. The cannula according to claim 1, wherein the fastener comprises:
at least one protrusion extending from a periphery of the second clamping surface, the protrusion being configured for at least one of the side branch and the suture to be wrapped around the protrusion; and
at least one notch disposed on a periphery of the second clamping surface.
6. The cannula according to claim 5, wherein the at least one notch is disposed adjacent to the at least one protrusion.
7. A cannula comprising:
a first clamping surface;
a second clamping surface opposed to the first clamping surface,
the second clamping surface including a first circumferential portion and a second circumferential portion, and
the first circumferential portion and the second circumferential being rotatable about a first hinge to surround a length of vasculature such that a portion of the vasculature can pass between the first circumferential portion and the second circumferential portion and at least partially through the first clamping surface;

at least one strap configured to wrap around the cannula to retain the first clamping surface and the second clamping surface in a closed position; and at least two posts attaching the at least one strap to the cannula.

8. The cannula according to claim 7, wherein the at least two posts are disposed approximately ninety degrees apart from one another around a surface of the cannula.

9. The cannula according to claim 7, wherein the at least two posts attach the at least one strap to the cannula without an adhesive.

10. A cannula comprising:

a first clamping surface;

a second clamping surface opposed to the first clamping surface,
  the second clamping surface including a first circumferential portion and a second circumferential portion, and
  the first circumferential portion and the second circumferential being rotatable about a first hinge to surround a length of vasculature such that a portion of the vasculature can pass between the first circumferential portion and the second circumferential portion and at least partially through the first clamping surface;

a tissue supporting surface disposed outside of the second clamping surface and being configured to retain tissue outside of the first clamping surface and the second clamping surface; and a stiffening rib that stiffens the tissue supporting surface.

11. The cannula according to claim 10, wherein the tissue supporting surface comprises serrations or knurls.

12. The cannula according to claim 10, further comprising a strap to restrain the cannula in a closed position,
  wherein the stiffening rib comprises a recess configured to limit lateral movement of the strap.

13. A cannula comprising:

a first clamping surface comprising a flexible material;

a second clamping surface opposed to the first clamping surface,
  the second clamping surface including a first circumferential portion and a second circumferential portion, and
  the first circumferential portion and the second circumferential being rotatable about a first hinge to surround a length of vasculature such that a portion of the vasculature can pass between the first circumferential portion and the second circumferential portion and at least partially through the first clamping surface; and a chamber portion that includes a chamber, an opening, and a seal engaging portion disposed around the opening,
  the seal engaging portion being engaged with and supporting a periphery of the first clamping surface, and
  at least one support being disposed within the chamber, the support supporting the first clamping surface and being disposed closer to a center of the first clamping surface than the seal engaging portion.

14. The cannula according to claim 13, wherein the at least one support comprises a plurality of supports, the plurality of supports each being spaced equally and radially about the center of the first clamping surface.

15. The cannula according to claim 13, wherein the at least one support is attached to and extends from a wall of the chamber.

16. The cannula according to claim 1, wherein:

the first circumferential portion and the second circumferential portion are rotated about the first hinge around a first axis, the first clamping surface and the second clamping surface are rotatable about a second hinge around a second axis, and the first axis is perpendicular to the second axis.

* * * * *